United States Patent
Yamada et al.

(10) Patent No.: US 8,471,211 B2
(45) Date of Patent: Jun. 25, 2013

(54) TWO-DIMENSIONAL POSITION MAP CORRECTING METHOD, AND RADIATION DETECTING APPARATUS

(75) Inventors: Yoshihiro Yamada, Kyoto (JP); Nobuya Hashizume, Kyoto (JP); Masanobu Sato, Kizugawa (JP); Keishi Kitamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 287 days.

(21) Appl. No.: 12/918,595

(22) PCT Filed: May 19, 2008

(86) PCT No.: PCT/JP2008/059146
§ 371 (c)(1),
(2), (4) Date: Aug. 20, 2010

(87) PCT Pub. No.: WO2009/141861
PCT Pub. Date: Nov. 26, 2009

(65) Prior Publication Data
US 2010/0327168 A1     Dec. 30, 2010

(51) Int. Cl.
*G01D 18/00*     (2006.01)
*G01T 1/20*     (2006.01)
*G01T 1/164*     (2006.01)
*G21K 1/02*     (2006.01)

(52) U.S. Cl.
USPC ............. 250/363.09; 250/252.1; 250/362; 250/363.01; 250/363.02

(58) Field of Classification Search
USPC ............ 250/362, 252.1, 363.01–363.1
See application file for complete search history.

(56) References Cited

U.S. PATENT DOCUMENTS

2007/0252079 A1*  11/2007  Wang et al. ............ 250/252.1
2008/0128631 A1*  6/2008   Suhami ................. 250/370.09

FOREIGN PATENT DOCUMENTS

JP     2005-43104 A    2/2005

* cited by examiner

*Primary Examiner* — Michael G Lee
*Assistant Examiner* — Laura Gudorf
(74) *Attorney, Agent, or Firm* — Cheng Law Group, PLLC

(57) ABSTRACT

A radiation detecting apparatus of this invention includes an arithmetic processing device which carries out arithmetic processes for drawing boundaries based on peaks of signal strengths and separating respective positions by the boundaries, and for determining, by using spatial periodicity of the peaks, the number of peaks having failed to be separated, with a plurality of peaks connecting to each other. If the separation fails with a plurality of peaks connecting to each other, the number of peaks in error is determined using spatial periodicity of the peaks. Thus, by using spatial periodicity of the peaks, the number of peaks in error can be determined and boundaries can be set easily. As a result, incident positions can also be discriminated easily, and detecting positions of radiation can be determined easily.

7 Claims, 7 Drawing Sheets

TWO-DIMENSIONAL POSITION MAP CORRECTING METHOD, AND RADIATION DETECTING APPARATUS

TECHNICAL FIELD

This invention relates to a two-dimensional position map correcting method, and a radiation detecting apparatus, for correcting a two-dimensional position map used when detecting radiation with radiation detectors each including a plurality of scintillator elements and a light sensor optically connected thereto.

BACKGROUND ART

A PET (Positron Emission Tomography) apparatus will be described as an example of nuclear medicine diagnostic apparatus, i.e. ECT (Emission Computed Tomography) apparatus. The PET apparatus is constructed to detect a plurality of γ-rays generated by annihilation of positrons, and to reconstruct a sectional image of a patient only when a plurality of detectors simultaneously detect the γ-rays.

Specifically, a patient is medicated with a radioactive drug including a positron-emitting radionuclide, and detectors consisting of numerous detecting element (e.g. scintillator) groups detect pair annihilation γ-rays of 511 KeV released from the patient medicated. And when two detectors detect γ-rays within a definite period of time, they are counted as one pair of annihilation γ-rays detected as a coincidence, and a pair annihilation generating point is determined to exist on a straight line linking the detector pair having detected them. Such coincidence information is accumulated and reconstruction is carried out to obtain a positron-emitting radionuclide distribution image (i.e. a sectional image).

At this time, image resolution of the sectional image is improved by increasing the number of scintillators to obtain more particular γ-ray detecting positions on the detectors, combining them with photomultiplier tubes (PMT) capable of detecting positions, and discriminating γ-ray detecting positions as individual scintillator elements to increase γ-ray detecting accuracy. So, the number of scintillators is increased to increase discriminating capability. In recent years, in particular, DOI detectors have been developed, which have scintillators laminated also in a depth direction to be capable of discriminating light source positions having caused interaction in the depth direction (DOI: Depth of Interaction).

To discriminate γ-ray incident positions, a two-dimensional position map prepared beforehand is used. The two-dimensional position map is drawn by centroid calculation of electric signals acquired with light sensors represented by position detecting type photomultiplier tubes, to calculate two-dimensional coordinates (X, Y) relating to events of detecting γ-rays. Further, this two-dimensional position map is obtained by emitting γ-rays in uniform parallel beams to the detectors, repeating the above operation while the γ-rays are detected, and integrating two-dimensional coordinates on a two-dimensional plane. These are drawn as a distribution with peaks corresponding to respective positions of scintillator elements (crystal elements). FIG. 9 shows a two-dimensional position map in the case of a DOI detector having four layers of scintillators laminated in the depth direction. The positions indicated by white circles (shown as "○" in FIG. 9) are scintillators in the first layer (written "1st Layer" in FIG. 9). The positions indicated by white rhombuses are scintillators in the second layer (written "2nd Layer" in FIG. 9). The positions indicated by white double octagons are scintillators in the third layer (written "3rd Layer" in FIG. 9). The positions indicated by white rectangles (shown as "□" in FIG. 9) are scintillators in the fourth layer (written "4th Layer" in FIG. 9). Incident positions of actually incident γ-rays can be discriminated by referring to a look-up table (LUT) having each position in the two-dimensional position map corresponding to each scintillator, and referring to the two-dimensional position map.

Incidentally, where a plurality of scintillators are arranged in three dimensions as in the DOI detector, diffusion is provided by combination of a light reflective material and a light transmissive material, for example, between adjoining scintillators, so that positions do not overlap in the two-dimensional position map. Further, a technique of correcting the two-dimensional position map has been introduced, which carries out a statistical clustering process in order to increase the discriminating capability still further (see Patent Document 1, for example).

On an actual two-dimensional position map, peaks of signal strength appear in a grid form. If to which of the positions (rows and columns) on the two-dimensional position map a peak belongs is known, it is possible to discriminate which scintillator element (crystal) in a scintillator block (crystal block) incidence has occurred, and whether light has been emitted from that crystal. Therefore, it is necessary to set boundaries for area division of the entire two-dimensional position map into spheres of influence of respective peaks. As a result, each point on the screens of light sensors is in the sphere of influence of one of the peaks.

Patent Document 1

Unexamined Patent Publication No. 2005-43104

DISCLOSURE OF THE INVENTION

Problem to be Solved by the Invention

However, one detector is formed of several hundreds to several thousands of crystals (scintillator elements), and the corresponding number of peaks will appear on an image. Inputting boundaries of the two-dimensional position map manually requires great time and effort. It is therefore desirable to set boundaries by automation, but errors often occur in determining boundaries because peaks are not fully separated in peripheral portions of the two-dimensional position map.

This invention has been made having regard to the state of the art noted above, and its object is to provide a two-dimensional position map correcting method and a radiation detecting apparatus which can set boundaries easily.

Means for Solving the Problem

To fulfill the above object, this invention provides the following construction.

A two-dimensional position map correcting method of this invention is a two-dimensional position map correcting method used when detecting with radiation detectors each formed of a plurality of scintillator elements arranged in one dimension, two dimensions or three dimensions, and a light sensor optically coupled thereto, for correcting a two-dimensional position map presenting, in two dimensions, signal strengths obtained with the light sensor as corresponding to incident positions of the radiation incident on the scintillator elements, the two-dimensional position map correcting method comprising a peak separating step for drawing boundaries based on peaks of the signal strengths, and separating respective positions by the boundaries, and a number determining step for determining, by using spatial periodicity of the peaks, the number of peaks having failed to be separated in the peak separating step, with a plurality of the peaks connecting to each other.

According to the two-dimensional position map correcting method of this invention, a peak separating step is provided for drawing boundaries based on peaks of the signal strengths, and separating respective positions by the boundaries. If the separation in the peak separating step fails with a plurality of peaks connecting to each other, a number determining step determines the number of peaks in error using spatial periodicity of the peaks. Thus, by using spatial periodicity of the peaks, the number of peaks in error can be determined and boundaries can be set easily.

In the two-dimensional position map correcting method of this invention, it is preferable to comprise a boundary determining step for separating respective positions having failed to be separated in the peak separating step, by setting the boundaries so that a sensitivity ratio of each of the scintillator elements and a total ratio of pixels in a peak area be in agreement. Using the fact that sensitivity ratio and pixel value are in a proportional relationship, and supposing a sensitivity ratio for each scintillator element is known beforehand, it is possible to set a boundary so that the sensitivity ratio for each scintillator element and the total ratio of pixels in the peak area be in agreement, in order to separate respective positions having failed to be separated in the peak separating step.

The above separating step may be executed to compare the signal strengths and obtain respective local minimal values, and to draw positions of the local minimal values as the boundaries, and separate the respective positions by the boundaries, or may be executed to compare the signal strengths and obtain respective local maximal values, and to draw positions of the local maximal values as the boundaries, and separate the respective positions by the boundaries. When the peaks are considered to be local maximal, positions of local minimal values substantially correspond to the boundaries. Thus, as in the former, the positions of local minimal values are drawn as boundaries, and the respective positions are separated by the boundaries.

A radiation detecting apparatus of this invention is a radiation detecting apparatus having radiation detectors each formed of a plurality of scintillator elements arranged in one dimension, two dimensions or three dimensions, and a light sensor optically coupled thereto, the apparatus comprising a storage device, in relation to a two-dimensional position map presenting, in two dimensions, signal strengths obtained with the light sensor as corresponding to incident positions of the radiation incident on the scintillator elements, for storing a table having, in a corresponding relationship, each position in the two-dimensional position map and each scintillator element, and an arithmetic processing device for carrying out arithmetic processes for correcting the two-dimensional position map, radiation detecting positions being determined by discriminating the incident positions based on the two-dimensional position map corrected and results of radiation detection, wherein the arithmetic processing device has a peak separating step for drawing boundaries based on peaks of the signal strengths, and separating respective positions by the boundaries, and a number determining step for determining, by using spatial periodicity of the peaks, the number of peaks having failed to be separated in the peak separating step, with a plurality of the peaks connecting to each other, and carries out arithmetic processes relating to these steps.

According to the radiation detecting apparatus of this invention, the arithmetic processing device has a peak separating step for drawing boundaries based on peaks of the signal strengths, and separating respective positions by the boundaries, and a number determining step for determining, by using spatial periodicity of the peaks, the number of peaks having failed to be separated in the peak separating step, with a plurality of peaks connecting to each other, and carries out arithmetic processes relating to these steps. If the separation in the peak separating step fails with a plurality of peaks connecting to each other, the number determining step determines the number of peaks in error using spatial periodicity of the peaks. Thus, by using spatial periodicity of the peaks, the number of peaks in error can be determined and boundaries can be set easily. As a result, incident positions can also be discriminated easily, and detecting positions of radiation can be determined easily.

EFFECTS OF THE INVENTION

With the two-dimensional position map correcting method and radiation detecting apparatus according to this invention, a peak separating step is provided for drawing boundaries based on peaks of the signal strengths, and separating respective positions by the boundaries, and a number determining step for determining, by using spatial periodicity of the peaks, the number of peaks having failed to be separated in the peak separating step, with a plurality of the peaks connecting to each other. Arithmetic processes relating to these steps are carried out. If the separation in the peak separating step fails with a plurality of peaks connecting to each other, the number determining step determines the number of peaks in error using spatial periodicity of the peaks. Thus, by using spatial periodicity of the peaks, the number of peaks in error can be determined and boundaries can be set easily.

DESCRIPTION OF REFERENCES

3 ... γ-ray detectors
10 ... look-up table
13 ... two-dimensional position map correcting unit
31 ... scintillator block
32 ... photomultiplier tube (PMT)
M ... two-dimensional position map

EMBODIMENT

Figure 1:
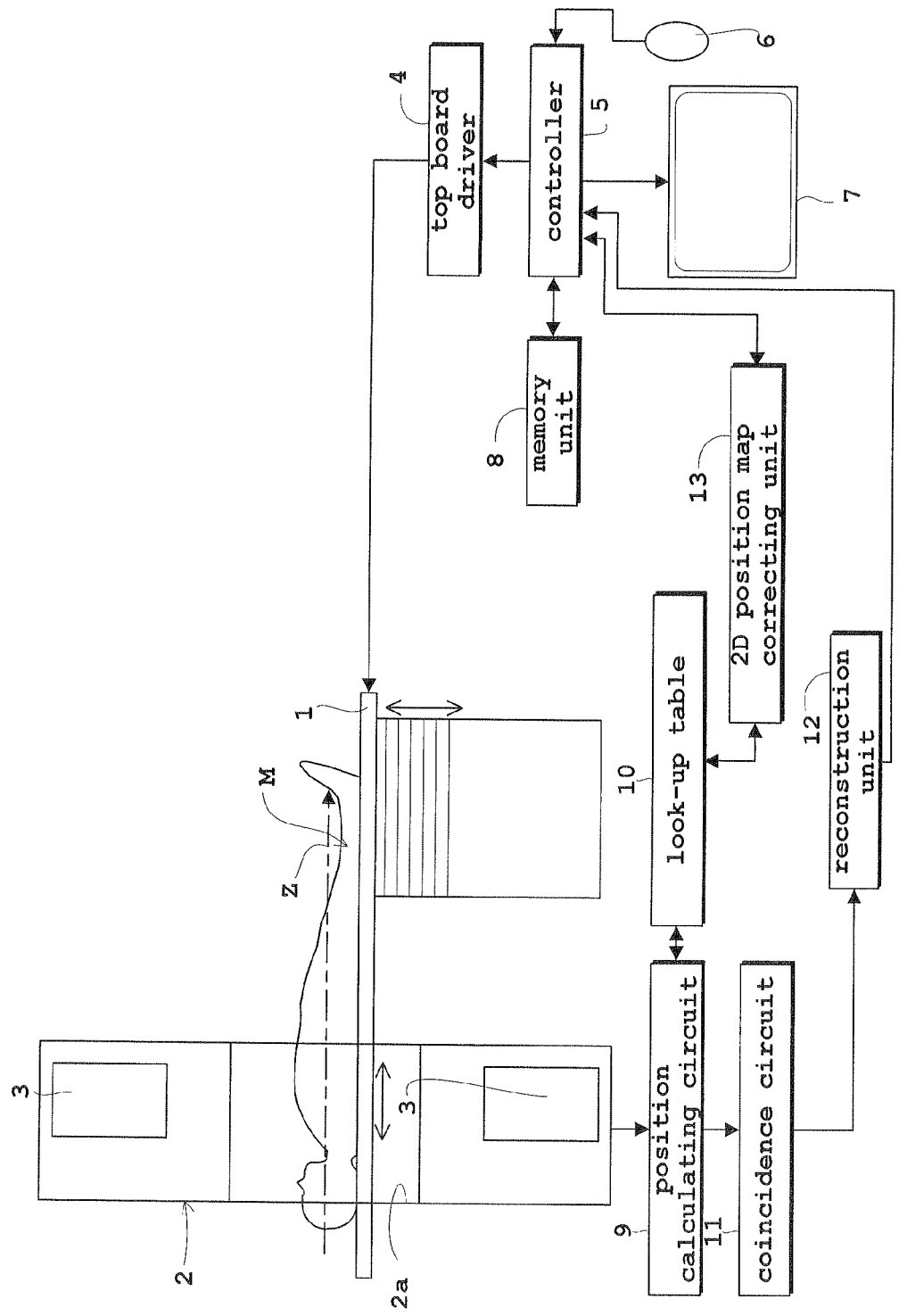
FIG. 1 is a side view and block diagram of a PET (Positron Emission Tomography) apparatus according to an embodiment.
Figure 2:
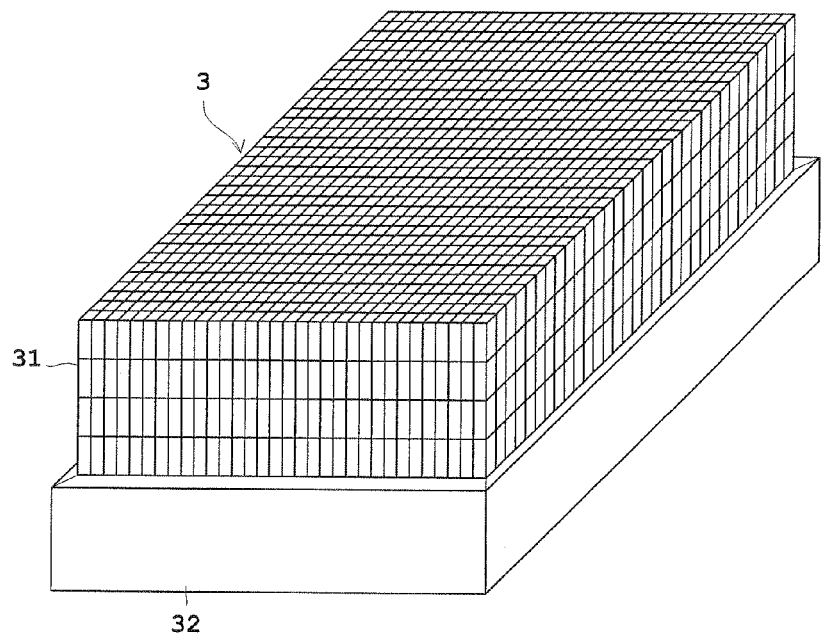
FIG. 2 is a schematic perspective view of a γ-ray detector.
Figure 3:
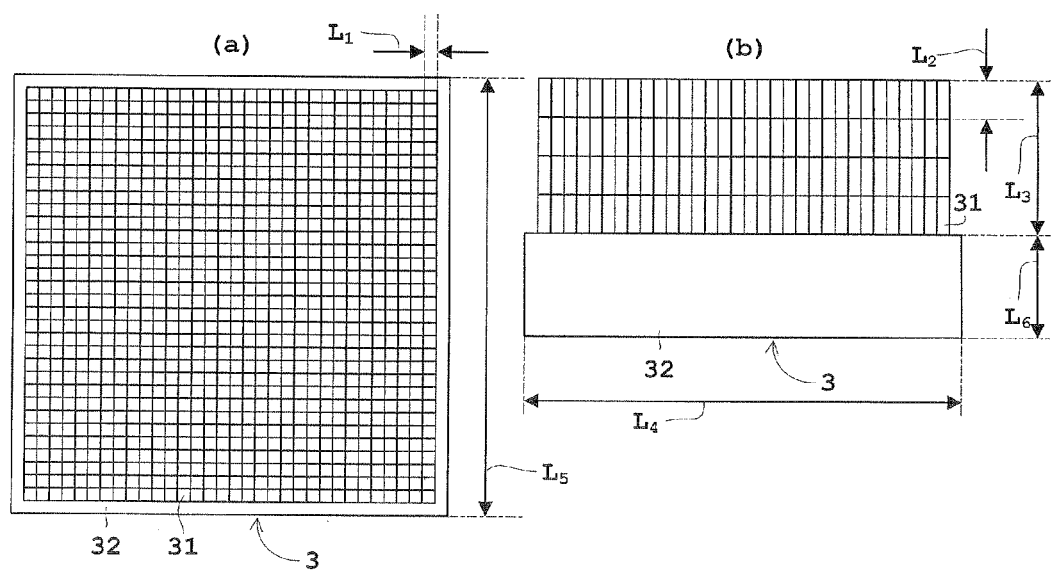
FIG. 3 (*a*) is a plan view of the γ-ray detector, and (*b*) is a side view of the γ-ray detector.

An embodiment of this invention will be described hereinafter with reference to the drawings. FIG. 1 is a side view and block diagram of a PET (Positron Emission Tomography) apparatus according to the embodiment. FIG. 2 is a schematic perspective view of a γ-ray detector. FIG. 3 (a) is a plan view of the γ-ray detector. FIG. 3 (b) is a side view of the γ-ray detector.

The PET apparatus according to this embodiment, as shown in FIG. 1, includes a top board 1 for supporting a patient M. This top board 1 is constructed to move up and down and make parallel translation along the body axis Z of the patient M. With this construction, the patient M placed on the top board 1 passes through an opening 2a of a gantry 2 described hereinafter, to be scanned in order from the head to the abdomen and the feet, to obtain images of the patient M. There is no limitation as to the sites scanned or the scanning sequence of the respective sites.

The PET apparatus according to this embodiment includes the gantry 2 with the opening 2a and γ-ray detectors 3, besides the top board 1. The γ-ray detectors 3 are arranged in a ring form so as to surround the body axis Z of the patient M, and are embedded in the gantry 2. The γ-ray detectors 3 correspond to the radiation detectors in this invention.

In addition, the PET apparatus according to this embodiment includes a top board driver 4, a controller 5, an input unit 6, an output unit 7, a memory unit 8, a position calculating circuit 9, a look-up table 10, a coincidence circuit 11, a reconstruction unit 12 and a two-dimensional position map correcting unit 13. The top board driver 6 is a mechanism for driving the top board 1 to make the above movements, and has a motor not shown. The look-up table 10 corresponds to the storage device in this invention. The two-dimensional position map correcting unit 13 corresponds to the arithmetic processing device in this invention. The gantry 2, γ-ray detectors 3, position calculating circuit 9, look-up table 10, coincidence circuit 11 and two-dimensional position map correcting unit 13 constitute the radiation detecting apparatus in this invention.

The controller 5 performs overall control of the components forming the PET apparatus according to this embodiment. The controller 5 includes a central processing unit (CPU) and others.

The input unit 6 feeds the controller 5 with data and commands inputted by the operator. The input unit 6 includes a pointing device represented by a mouse, keyboard, joystick, trackball and/or touch panel. The output unit 7 includes a display unit represented by a monitor, a printer, and so on.

The memory unit 8 and look-up table 10 are formed of storage media represented by a ROM (Read-only Memory), RAM (Random-Access Memory) and the like. In this embodiment, a count of coincidences counted by the coincidence circuit 11 and images processed by the reconstruction unit 12 are written and stored in a RAM, and are read from the RAM as necessary. In this embodiment, in particular, a two-dimensional position map showing, in two dimensions, electric signals acquired from photomultiplier tubes 33 (see FIGS. 2 and 3) described hereinafter, which are put to centroid calculations and made to correspond to positions of scintillator elements of scintillator blocks 31 (see FIGS. 2 and 3) described hereinafter, is written and stored in the look-up table 10 as a table having each position in the two-dimensional position map and each scintillator element in a corresponding relationship, which is read from the look-up table 10 at a time of correction of the two-dimensional position map by the two-dimensional position map correcting unit 13, and the two-dimensional position map is rewritten and corrected. Programs for carrying out various types of nuclear medicine diagnosis and arithmetic processes by the two-dimensional position map correcting unit 13 are stored beforehand in a ROM. With the controller 5 executing the programs, the nuclear medicine diagnosis and arithmetic processes by the two-dimensional position map correcting unit 13 according to the programs are carried out.

The reconstruction unit 12 and two-dimensional position map correcting unit 13 are realized by the controller 5 executing, for example, a program stored in the ROM of the storage medium represented by the above memory unit 8, or the commands inputted with a pointing device represented by the input unit 6.

The scintillator blocks 31 (see FIGS. 2 and 3) of the γ-ray detectors 3 convert into light the γ-rays generating from the patient M medicated with a radioactive drug. The photomultiplier tubes (PMT) 32 (see FIGS. 2 and 3) of the γ-ray detectors 3 multiply the converted light and convert it into electric signals. The electric signals are fed to the position calculating circuit 9 as image information (pixel values, i.e. a count of coincidences counted by the γ-ray detectors 3).

The position calculating circuit 9 refers to the look-up table 10 and refers to the two-dimensional position map at a time of nuclear medicine diagnosis, and determines which scintillator elements of the scintillator blocks 31 (see FIGS. 2 and 3) the count has occurred from. Specifically, incident positions on the scintillator elements are determined from a centroid calculation carried out at every incidence. The incident positions and counts (image information) obtained are fed to the coincidence circuit 11.

Specifically, when the patient M is medicated with a radioactive drug, two γ-rays are generated by annihilation of positrons of positron emission type RI. The coincidence circuit 11 checks positions of the scintillator blocks 31 (see FIGS. 2 and 3) (more particularly, positions of incidence on the scintillator elements) and incidence timing of the γ-rays, and determines received image information to be proper data only when the γ-rays are incident on two scintillator blocks 31 at opposite sides of the patient M at the same time. The coincidence circuit 11 ignores γ-rays incident only on one scintillator block 31.

Image information fed to the coincidence circuit 11 is fed as projection data to the reconstruction unit 12. The reconstruction unit 12 reconstructs the projection data to obtain images of the patient M. The images are fed to the output unit 7 through the controller 5. In this way, nuclear medicine diagnosis is carried out based on the images obtained by the reconstruction unit 12.

A γ-ray detector 3, as shown in FIGS. 2 and 3, includes a scintillator block 31 formed of a plurality of scintillator elements, and a photomultiplier tube (hereinafter abbreviated simply as "PMT") 32 optically coupled to the scintillator block 31. Each scintillator element forming the scintillator block 31 emits light with incidence of a γ-ray, thereby converting the γ-ray into light. The scintillator element detects the γ-ray by this conversion. The light emitted from the scintillator elements is fully diffused in the scintillator block 31, and is inputted to the PMT 32. The PMT 32 multiplies the light converted by the scintillator block 31, and converts it into electric signals. The electric signals are fed as image information (pixel values) to the position calculating circuit 9 (see FIG. 1) and also to the coincidence circuit 11 (see FIG. 1) as described above. The scintillator elements forming the scintillator block 31 correspond to the scintillator elements in this invention. The photomultiplier tube (PMT) 32 corresponds to the light sensor in this invention.

As shown in FIG. 3, one side of a scintillator element is set to $L_1$, the height of a scintillator element to $L_2$, the height of the scintillator block 31 to $L_3$, the width in the transverse direction of PMT 32 to $L_4$, the width in the longitudinal direction of PMT 32 to $L_5$, and the height of PMT 32 to $L_6$. This embodiment uses γ-ray detectors 3 of $L_1$=1.45 mm, $L_2$=4.5 mm, $L_3$=18 mm, $L_4$=52 mm, $L_5$=49.5 mm, and $L_6$=12.4 mm. Of course, each size of the γ-ray detectors 3 is not limited to this. This embodiment uses γ-ray detectors 3 with the scintillator block 31 having scintillator elements arranged in 32×32×4 layers, and the PMT 32 with 16×16 multi-anodes. There is no limitation as to the number of scintillator elements forming the scintillator block 31 or the number of multi-anodes of PMT 32.

Figure 4:
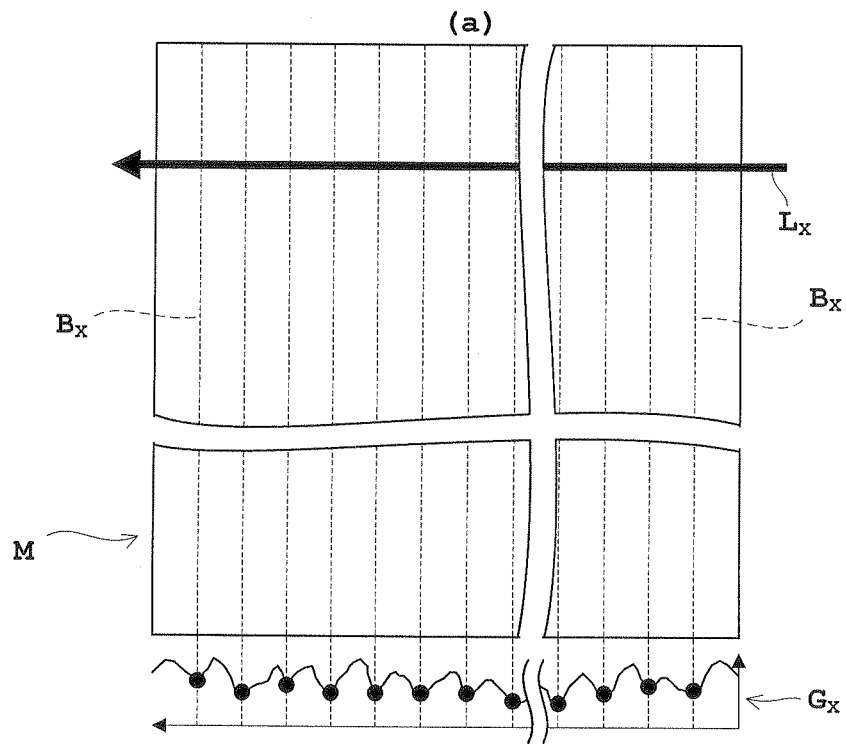
FIG. 4 (*a*) is a plan view of a two-dimensional position map for use in description of determining local minimal values in the direction of rows (x), and (*b*) is a plan view of the two-dimensional position map for use in description of determining local minimal values in the direction of columns (y)
Figure 4:
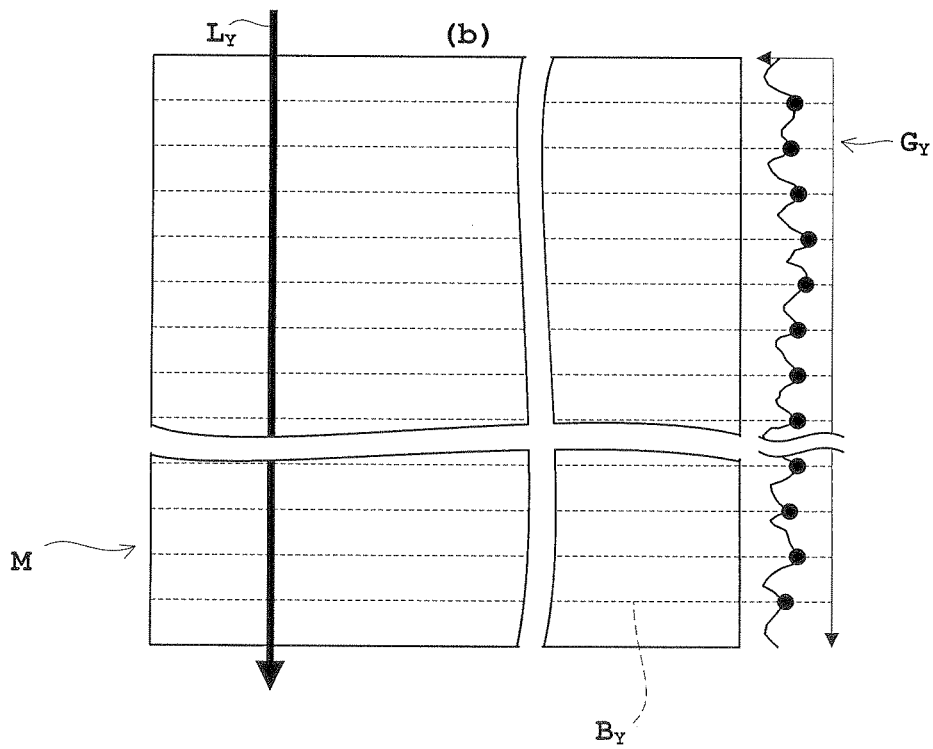
Figure 5:
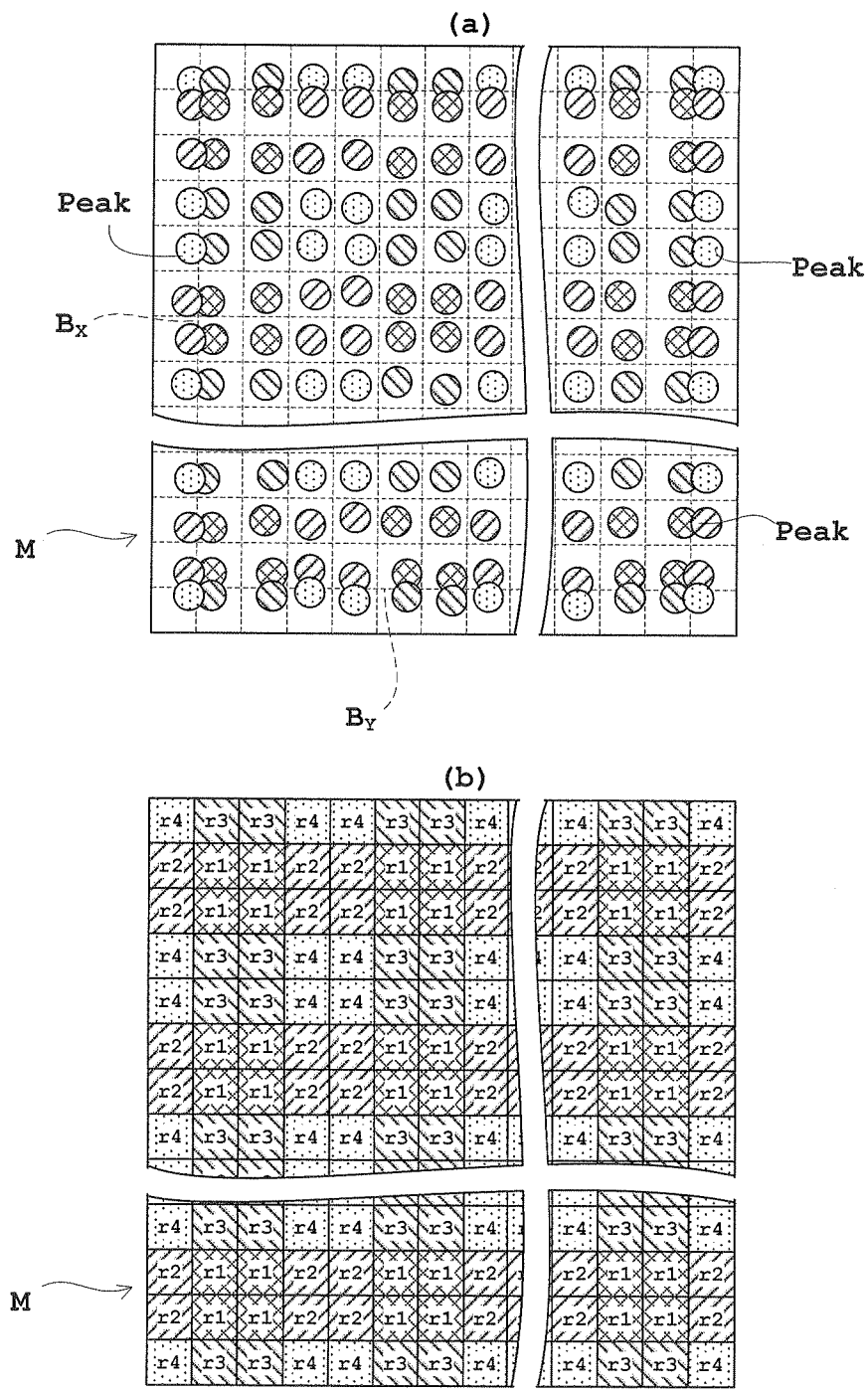
FIG. 5 (*a*) is a plan view of the two-dimensional position map schematically showing peaks, and (*b*) is a plan view of the two-dimensional position map presenting a sensitivity ratio for each scintillator element and representing spatial periodicity of the peaks.
Figure 6:
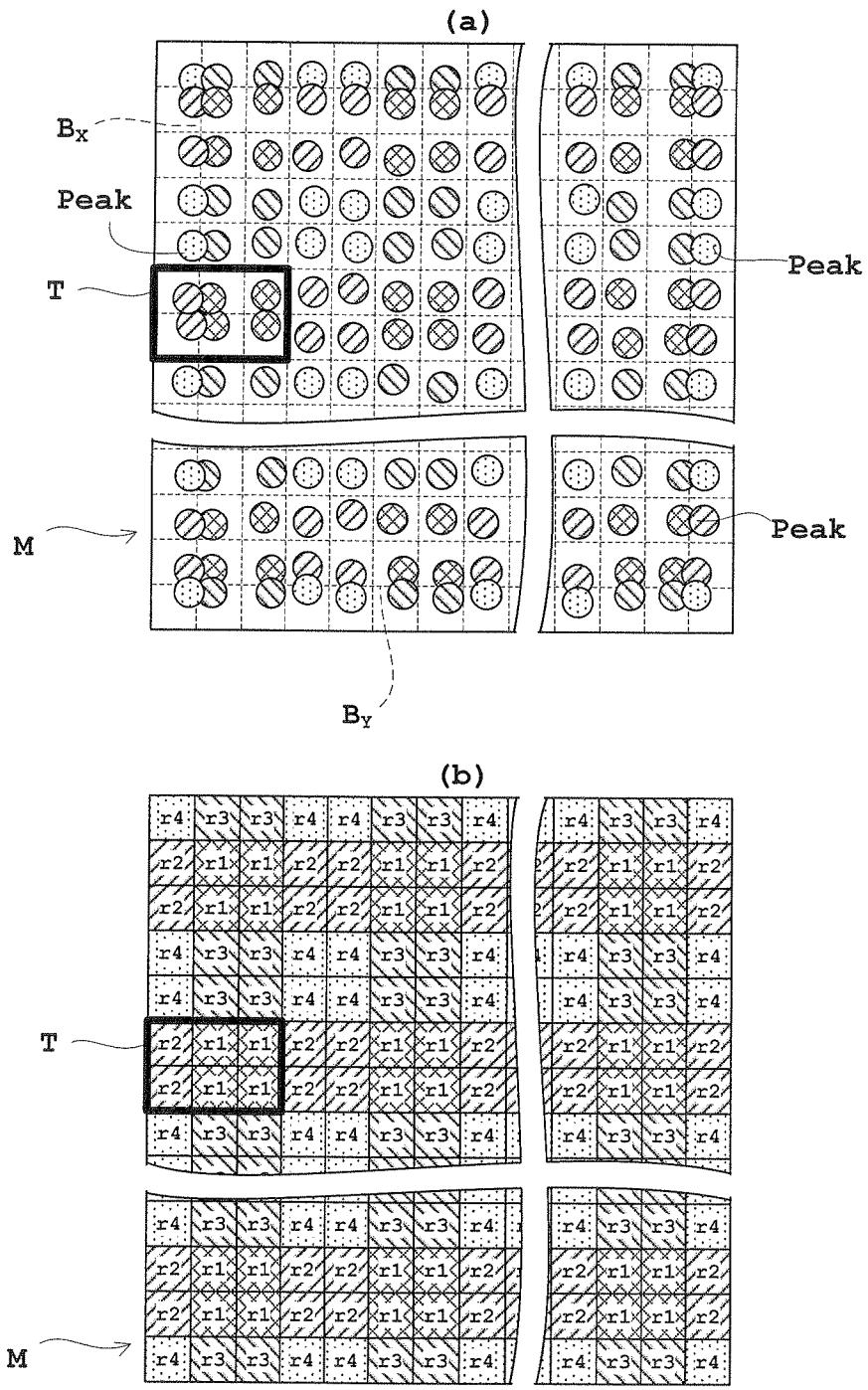
FIG. 6 (*a*) is a plan view of the two-dimensional position map schematically showing peaks in the case of separating an area targeted when separation has failed, and (*b*) is a plan view of the two-dimensional position map presenting a sensitivity ratio for each scintillator element and representing spatial periodicity of the peaks in the case of separating the area targeted when separation has failed.
Figure 7:
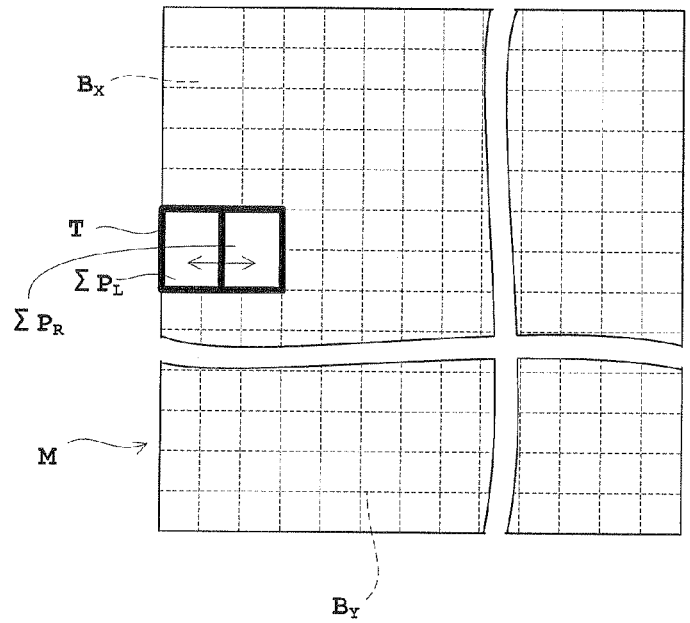
FIG. 7 is a plan view of the two-dimensional position map for use in description of setting boundaries in the case of separating the area targeted when separation has failed.
Figure 8:
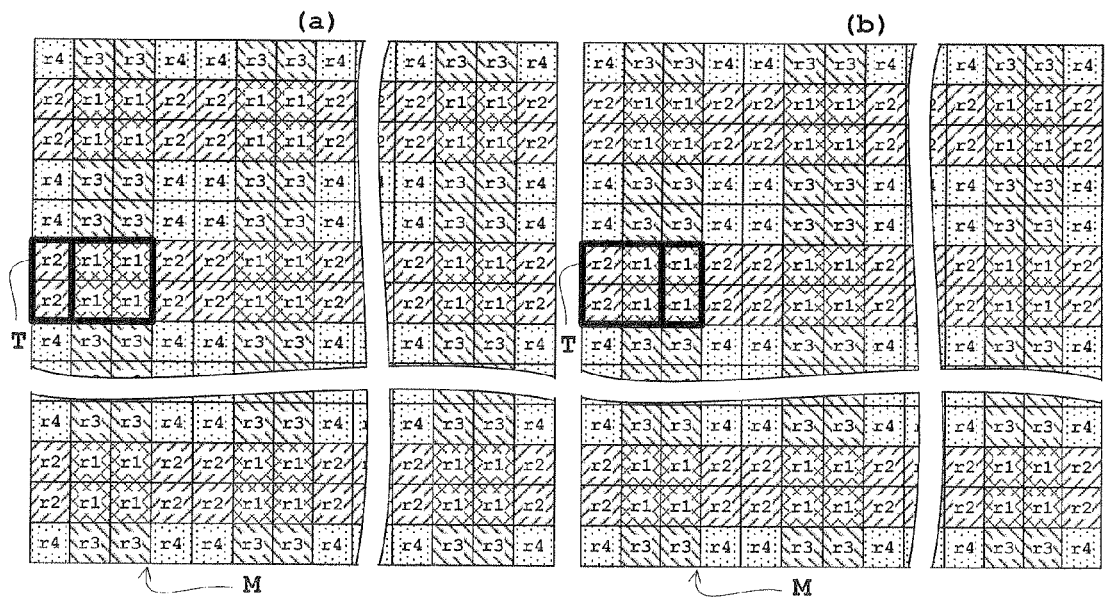
FIGS. 8 (*a*) and (*b*) are plan views of the two-dimensional position map presenting sensitivity ratios for use in description of setting boundaries in the case of separating the area targeted when separation has failed.

Next, arithmetic processes by the two-dimensional position map correcting unit 13 will be described with reference to FIGS. 4-8. FIG. 4 (a) is a plan view of a two-dimensional position map for use in description of determining local minimal values in the direction of rows (x). FIG. 4 (b) is a plan view of the two-dimensional position map for use in description of determining local minimal values in the direction of columns (y). FIG. 5 (a) is a plan view of the two-dimensional position map schematically showing peaks. FIG. 5 (b) is a plan view of the two-dimensional position map presenting a sensitivity ratio for each scintillator element representing spatial periodicity of the peaks. FIG. 6 (a) is a plan view of the two-dimensional position map schematically showing peaks in the case of separating an area targeted when separation has failed. FIG. 6 (b) is a plan view of the two-dimensional position map presenting a sensitivity ratio for each scintillator element representing spatial periodicity of the peaks in the case of separating the area targeted when separation has failed. FIG. 7 is a plan view of the two-dimensional position map for use in description of setting boundaries in the case of separating the area targeted when separation has failed. FIG. 8 is a plan view of the two-dimensional position map presenting sensitivity ratios for use in description of setting boundaries in the case of separating the area targeted when separation has failed.

Figure 9:
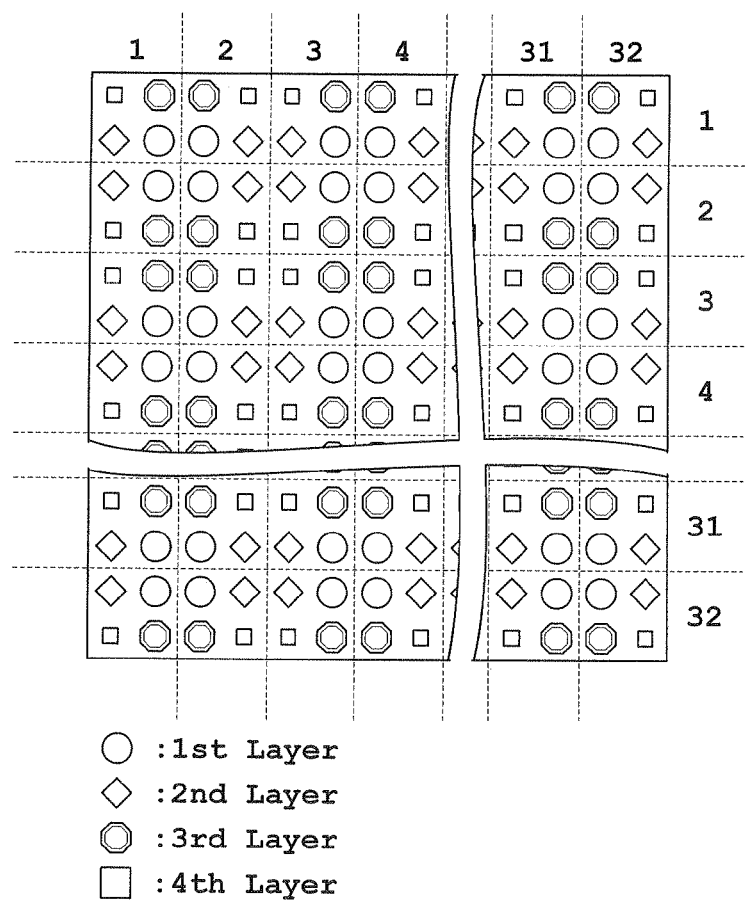
FIG. 9 is a plan view of a two-dimensional position map in the case of a DOI detector having four layers of scintillators laminated in a depth direction.

A two-dimensional position map is inputted (see FIG. 9). Specifically, after an Na-22 radiation source carries out uniform irradiation from above the γ-ray detectors 3 to obtain a two-dimensional position map and before carrying out an actual nuclear medicine diagnosis, a table is prepared by carrying out area division and labeling the entire map with location numbers of the scintillator elements, and is written and stored in the look-up table 10. In this embodiment, the two-dimensional position map is an image of 1024×1024 pixels, and the look-up table (LUT) has location numbers of the scintillator elements in the arrangement of 1024×1024. That is, on the look-up table (LUT), the respective positions (1024×1024 pixels) in the two-dimensional position map and the respective scintillator elements are in correspondence to one another.

The scintillator block 31 (i.e. crystal block) forming the γ-ray detector 3 is made by assembling numerous (32×32×4 in this embodiment) scintillator elements (i.e. small crystals). The number of peaks of pixel values is determined by a total of the small crystals forming the crystal block. It is assumed hereinafter regarding the total of peaks that, of the rows and columns forming the two-dimensional position map, the number along the rows is $N_X$ and the number along the columns is $N_Y$. Therefore, the total of peaks is $N_X \times N_Y$. As shown in FIG. 5 (a), the shading (pixel values) of peaks Peak changes in a spatially periodic way. This results from differences in sensitivity of different layers of the block, and its cycle is dependent on the number of layers of the small crystals. Hereinafter, this cycle or number of layers is assumed to be t. In this embodiment, as noted above, $N_X$=$N_Y$=64 and t=4.

In the two-dimensional position map M, the pixel values which are signal strengths are compared, and respective local minimal values or local maximal values are obtained. Positions of these local minimal values or local maximal values are drawn as boundaries, and the respective positions are separated by the boundaries. In this embodiment, as shown in FIG. 4 (a), local minimal values are obtained along each line $L_X$ parallel to the direction of rows (x), to draw and set boundaries, and as shown in FIG. 4 (b), local minimal values are obtained along each line $L_Y$ parallel to the direction of columns (y), to draw and set boundaries.

Specifically, as shown in FIG. 4 (a), a graph $G_X$ is prepared with a horizontal axis representing line $L_X$ and a vertical axis representing the pixel values (that is, a profile of pixel values in the direction of rows). And points (depicted with "●" in FIG. 4) having local minimal values in the graph $G_X$ are selected. Boundaries $B_X$ are drawn in positions corresponding to the local minimal values with respect to the line $L_X$ in question. Assume that the respective positions are separated by these boundaries $B_X$ and peaks $M_X$ in number are selected in the direction of rows (x). Similarly, as shown in FIG. 4 (b), a graph $G_Y$ is prepared with a horizontal axis representing line $L_Y$ and a vertical axis representing the pixel values (that is, a profile of pixel values in the direction of columns). And points (depicted with "●" in FIG. 4) having local minimal values in the graph $G_X$ are selected. Boundaries $B_Y$ are drawn in positions corresponding to the local minimal values with respect to the line $L_Y$ in question. Assume that the respective positions are separated by these boundaries $B_Y$ and peaks $M_Y$ in number are selected in the direction of columns (y). The above selects peaks $M_X \times M_Y$ in number ($M_X < N_X$, $M_Y < N_Y$). This separating operation corresponds to the peak separating step in this invention.

It is understood that this separation leaves unseparated peaks ($N_X$–$M_X$) in number at the right and left in the direction of rows, and ($N_Y$–$M_Y$) in number at the top and bottom in the direction of columns. That is, peaks ($N_X$–$M_X$) in number and ($N_Y$–$M_Y$) in number connected to one another indicate that the separation has ended in failure. Assuming that the difference in number between right and left peaks having failed to be separated is less than t, the numbers ($N_L$, $N_R$) of right and left peaks having failed to be separated can be determined by comparing a pattern of the shading (i.e. pixel values). The same applies to the case of the separation having failed at the top and bottom.

Specifically, using the fact that sensitivity ratio and pixel value are in a proportional relationship, and supposing a sensitivity ratio for each scintillator element is known beforehand, the number of peaks can be determined by collating the sensitivity ratio with the pattern of shading (pixel values) of an image. The sensitivity ratio changes in a spatially periodic way as shown in FIG. 5 (b), and the shading (pixel values) of the image also changes in a spatially periodic way as shown in FIG. 5 (a) noted above. Assuming that, in the case of t=4, the sensitivity ratio of the first layer is r1, the sensitivity ratio of the second layer is r2, the sensitivity ratio of the third layer is r3, and the sensitivity ratio of the fourth layer is r4, the sensitivity ratios and the shading of the separated image shown in FIG. 5 (a) correspond to each other. Therefore, the number of peaks having failed to be separated can be determined using the spatial periodicity of the peaks.

The sensitivity ratio for each scintillator element may be derived beforehand from experiment, or use may be made of r1, r2, r3 and r4 derived from the sensitivity ratio of a central portion of the two-dimensional position map M.

FIG. 5 (a) is a view showing 62 peaks Peak selected in the direction of rows (x). That is, $M_X$=62. By comparing the peaks Peak of FIG. 5 (a) using the cycles of four shown in FIG. 5 (b), it is seen that, in the case of FIG. 5 (a), two end peaks Peak at the right and left are crushed by connection, and are determined to be one, respectively. Similarly, it is seen that, in the case of FIG. 5 (a), two end peaks Peak at the top and bottom are crushed by connection, and are determined to be one, respectively. This determining operation corresponds to the number determining step in this invention.

Re-separation of left-side peaks carried out when the separation has failed will be described using FIG. 6. A target area is depicted in thick-line frames and affixed with sign T in FIGS. 6-8. For expediency of description, it is assumed that, in FIG. 6 (a), as distinct from FIG. 5, the area T targeted when the separation has failed includes also two peaks Peak crushed by connection in the up-and-down direction, and are determined to be one. At this time, the sensitivity ratios of the area T targeted when the separation has failed are as shown in FIG. 6 (b). The sensitivity ratios of the area T targeted when the separation has failed are (r2, r1, r1, r2, r1, r1).

The boundaries (boundaries $B_X$ in FIGS. 6-8) in the area T (at the left end in FIGS. 6-8) targeted when the separation has failed are once erased as shown in FIG. 7. Together with the number of peaks crushed and unable to be separated from the start, left side $N_L$, and right side $N_R$, are assumed. For the end peaks $N_L$, and $N_R$, in number, boundaries are determined from the sensitivity ratios empirically known, to separate respective positions having failed to be separated, thereby separating the end peaks $N_L$, and $N_R$, in number.

As shown in FIG. 7, for example, a thick line is inserted to divide into right and left the area T targeted when the separation has failed. Assume that a total of pixels in a peak area to the left of the thick line is $\Sigma P_L$, and that a total of pixels in a peak area to the right of the thick line is $\Sigma P_R$. By setting a boundary so that the sensitivity ratio and the total ratio of the pixels in the peak areas be in agreement, the respective positions are separated to separate the peaks for the area T targeted when the separation has failed. For this purpose, the thick line dividing the area T into right and left is moved right and left in the directions of arrows in FIG. 7, and the thick line in a place where the sensitivity ratio and the total ratio of the pixels in the peak areas are in agreement is determined to be a boundary for re-separation.

When the sensitivity ratio is divided as (r2+r2):(r1+r1+r1+r1) as shown in FIG. 8 (a), for example, the thick line dividing the area T into right and left is moved right and left as shown in FIG. 7, to set a boundary which is the thick line, so that the sensitivity ratio and the total ratio of the pixels in the peak areas be in agreement, that is $\Sigma P_L$:$\Sigma P_R$=(r2+r2):(r1+r1+r1+r1). Similarly, when the sensitivity ratio is divided as (r2+r2+r1+r1):(r1+r1) as shown in FIG. 8 (b), the thick line dividing the area T into right and left is moved right and left as shown in FIG. 7, to set a boundary which is the thick line, so that the sensitivity ratio and the total ratio of the pixels in the peak areas be in agreement, that is $\Sigma P_L$:$\Sigma P_R$=(r2+r2+r1+r1):(r1+r1). When the area T is divided vertically, since the sensitivity ratio is the same for the upper and lower parts in FIGS. 6-8, a thick line vertically dividing the area T is moved up and down to set a boundary which is the thick line, so as to provide $\Sigma P_L$:$\Sigma P_R$=1:1, i.e. $\Sigma P_L$=$\Sigma P_R$. The same applies to the case of the right side and the cases of the top and bottom. The determination of this thick line (boundary) corresponds to the boundary determining step in this invention.

By carrying out the above operation, the two-dimensional position map correcting unit 13 prepares the look-up table by reading from the look-up table 10, and rewriting and correcting the two-dimensional position map.

With the radiation detecting apparatus (gantry 2, γ-ray detectors 3, position calculating circuit 9, look-up table 10, coincidence circuit 11 and two-dimensional position map correcting unit 13) provided for the PET apparatus according to this embodiment having above construction, the two-dimensional position map correcting unit 13 draws boundaries based on peaks of pixel values as signal strengths, and separates respective positions by the boundaries. If the separation fails with a plurality of peaks connecting to each other, the number of peaks in error is determined using spatial periodicity of the peaks. Therefore, by using spatial periodicity of the peaks, the number of peaks in error can be determined and boundaries can be set easily. As a result, incident positions can also be discriminated easily, and detecting positions of radiation (γ-rays in this embodiment) can be determined easily.

In this embodiment, it is preferable to separate respective positions having failed to be separated, by setting a boundary so that a sensitivity ratio for each scintillator element and a total ratio of pixels in a peak area be in agreement. Using the fact that sensitivity ratio and pixel value are in a proportional relationship, and supposing a sensitivity ratio for each scintillator element is known beforehand, it is possible to set a boundary so that the sensitivity ratio for each scintillator element and the total ratio of pixels in the peak area be in agreement, in order to separate respective positions having failed to be separated.

In this embodiment, pixel values which are signal strengths are compared to obtain respective local minimal values or local maximal values, and positions of these local minimal values or local maximal values are drawn as boundaries, and the respective positions are separated by the boundaries. When the peaks are considered to be local maximal, positions of local minimal values substantially correspond to the boundaries. Thus, as shown in FIG. 4, the positions of local minimal values are drawn as boundaries, and the respective positions are separated by the boundaries.

This invention is not limited to the foregoing embodiment, but may be modified as follows:

(1) In the foregoing embodiment, a PET apparatus has been described as an example of nuclear medicine diagnostic apparatus having the radiation detecting apparatus. This invention is applicable also to a SPECT (Single Photon Emission CT) apparatus which detects a single γ-ray to reconstruct a sectional image of a patient. It is applicable also to a PET-CT apparatus which is a combination of a PET apparatus and a CT apparatus. It is applicable also to radiation other than γ (e.g. α-rays, β-rays and so on).

(2) The foregoing embodiment provides DOI detectors each having a plurality of scintillator elements arranged in three dimensions. The invention is applicable also to radiation detectors each having a plurality of scintillator elements arranged in two dimensions or three dimensions.

(3) In the foregoing embodiment, the photomultiplier tubes (PMT) have been described as an example of light sensors. There is no limitation as long as light sensors are optically coupled to the scintillator elements, as exemplified by avalanche photodiodes and silicon photomultipliers.

The invention claimed is:

1. A two-dimensional position map correcting method used when detecting with radiation detectors each formed of a plurality of scintillator elements arranged in one dimension, two dimensions or three dimensions, and a light sensor optically coupled thereto, for correcting a two-dimensional position map presenting, in two dimensions, signal strengths obtained with the light sensor as corresponding to incident positions of the radiation incident on the scintillator elements, the two-dimensional position map correcting method comprising a peak separating step for drawing boundaries based on peaks of the signal strengths, and separating respective positions by the boundaries, and a number determining step for determining, by using spatial periodicity of the peaks, the number of peaks having failed to be separated in the peak separating step, with a plurality of the peaks connecting to each other.

2. The two-dimensional position map correcting method according to claim 1, comprising a boundary determining step for separating respective positions having failed to be separated in the peak separating step, by setting the boundaries so that as sensitivity ratio of each of the scintillator elements and a total ratio of pixels in a peak area be in agreement.

3. The two-dimensional position map correcting method according to claim 1, wherein the separating step is executed to compare the signal strengths and obtain respective local minimal values, and to draw positions of the local minimal values as the boundaries, and separate the respective positions by the boundaries.

4. The two-dimensional position map correcting method according to claim 1, wherein the separating step is executed to compare the signal strengths and obtain respective local maximal values, and to draw positions of the local maximal values as the boundaries, and separate the respective positions by the boundaries.

5. A radiation detecting apparatus having radiation detectors each formed of a plurality of scintillator elements arranged in one dimension, two dimensions or three dimensions, and a light sensor optically coupled thereto, the apparatus comprising a storage device, in relation to a two-dimensional position map presenting, in two dimensions, signal strengths obtained with the light sensor as corresponding to incident positions of the radiation incident on the scintillator elements, for storing a table having, in a corresponding relationship, each position in the two-dimensional position map and each scintillator element, and an arithmetic processing device for carrying out arithmetic processes for correcting the two-dimensional position map, radiation detecting positions being determined by discriminating the incident positions based on the two-dimensional position map corrected and results of radiation detection, wherein the arithmetic, processing device has a peak, separating step for drawing boundaries based on peaks of the signal strengths, and separating respective positions by the boundaries, and a number determining step for determining, by using spatial periodicity of the peaks, the number of peaks having failed to be separated in the peak separating step, with as plurality of the peaks connecting to each other, and carries out arithmetic processes relating to these steps.

6. The two-dimensional position map correcting method according to claim 2, wherein the separating step is executed to compare the signal strengths and obtain respective local minimal values, and to draw positions of the local minimal values as the boundaries, and separate the respective positions by the boundaries.

7. The two-dimensional position map correcting method according to claim 2, wherein the separating step is executed to compare the signal strengths and obtain respective local maximal values, and to draw positions of the local maximal values as the boundaries, and separate the respective positions by the boundaries.

* * * * *